United States Patent [19]

Vanlaer

[11] Patent Number: 5,565,021
[45] Date of Patent: Oct. 15, 1996

[54] PROCESS FOR TREATMENT OF WATER AND OF SURFACES IN CONTACT WITH THE SAID WATER IN ORDER TO PREVENT THE ATTACHMENT OF AND/OR TO REMOVE AND/OR TO CONTROL MACROORGANISMS, COMPOSITION AND PAINT FOR THE SAID TREATMENT

[76] Inventor: Antoine Vanlaer, 607 avenue de la République, 59000 Lille, France

[21] Appl. No.: 364,973

[22] Filed: Dec. 28, 1994

[30] Foreign Application Priority Data

Dec. 8, 1994 [FR] France .................. 94 14762

[51] Int. Cl.$^6$ ....................................... C09D 5/14
[52] U.S. Cl. ................ 106/18; 252/180; 514/674; 106/18.32
[58] Field of Search ................ 252/180, 384, 252/394; 106/14.15, 14.22, 14.24, 18, 18.32; 514/663, 673, 674; 422/6, 7, 16, 28; 210/764

[56] References Cited

U.S. PATENT DOCUMENTS

| | | | |
|---|---|---|---|
| 2,382,976 | 8/1945 | Coleman | 106/18.32 |
| 4,049,417 | 9/1977 | Witzel et al. | 106/18.32 |
| 4,212,674 | 7/1980 | Strauch | 106/14.24 |
| 4,304,590 | 12/1981 | Grade et al. | |
| 4,562,042 | 12/1985 | Moran | 106/14.24 |
| 5,236,493 | 8/1993 | Hunter et al. | 106/18.32 |
| 5,304,237 | 4/1994 | Barth et al. | 106/18.32 |
| 5,312,558 | 5/1994 | West | 106/18.32 |

FOREIGN PATENT DOCUMENTS

| | | | |
|---|---|---|---|
| 552575 | 2/1958 | Canada | 106/14.24 |
| 0017611 | 10/1980 | European Pat. Off. | |
| 0364271 | 4/1990 | European Pat. Off. | |
| 1601304 | 8/1970 | France | |
| 2701713 | 8/1994 | France | |
| 1961791 | 6/1971 | Germany | |
| 663172 | 4/1949 | United Kingdom | 106/14.24 |

*Primary Examiner*—Neil McCarthy
*Attorney, Agent, or Firm*—Cushman Darby & Cushman, L.L.P.

[57] ABSTRACT

The invention relates to a process for the treatment of water and of surfaces in contact with the said water in order to prevent the attachment and/or to remove and/or to control macroorganisms, in particular molluscs, on the said surfaces in contact with the water, in which process at least one biocidal and/or biostatic active product is employed which is injected into the water and/or applied to the said surfaces, according to which process the active product(s) used comprise(s) at least one polyamine of formula I:

$$R_1\text{-NH}[(CH_2)_3\text{-NH}]_n\text{-}(CH_2)_3NH_2 \qquad (I)$$

in which formula $R_1$ is a $C_8$–$C_{22}$ alkyl or alkenyl radical and at least one monoamine of formula II:

$$R_2NH_2 \qquad (II)$$

in which formula $R_2$ is a $C_{8-C22}$ alkyl or alkenyl radical, and n is an integer between 0 and 3 (inclusive).

The invention also relates to a composition to be injected into the water and to a paint for covering the surfaces in contact with the water.

7 Claims, No Drawings

PROCESS FOR TREATMENT OF WATER AND OF SURFACES IN CONTACT WITH THE SAID WATER IN ORDER TO PREVENT THE ATTACHMENT OF AND/OR TO REMOVE AND/OR TO CONTROL MACROORGANISMS, COMPOSITION AND PAINT FOR THE SAID TREATMENT

The present invention relates to a process for the treatment of water and of surfaces in contact with the latter in order to prevent the attachment of and/or to remove and/or to control macroorganisms, in particular-molluscs, on the surfaces in contact with water, to a composition to be injected into the water and to a paint to be applied to the surfaces in contact with the water, for the said treatment.

A considerable number of industries make use either of fresh water, such as water from streams, rivers, lakes, natural or artificial reservoirs, wells used in the ground or of other drawn water, or of salt water, such as sea-water. This water is, for example, used in boiler circuits or in cooling-water circuits. The water circulates in the industrial installations in an open circuit, the water being drawn, for example, from a river and subsequently discharged downstream, or in a closed or semi-closed circuit, the water being reused a number of times.

It is known that, on the surfaces of the installations in which the water circulates or is stored, micro-organisms first of all develop, which form on the said surfaces a biological or bacterial film consisting of organic materials, bacteria, algae, protozoa or other microorganisms. This biological film may lead to considerable losses in output, in heat exchangers for example. Moreover, the presence of this biological film may give rise to localized instances of corrosion, which are linked to the physical presence and to the metabolism of the microorganisms making up the said film. Subsequently, macroorganisms also develop on the surfaces in contact with water, which macroorganisms may be algae, molluscs such as mussels, clams and barnacles, serpulae, crustaceans, hydroids, bryozoa and hydrozoa. These macroorganisms form encrustments on the surfaces of the installations which are in contact with water. These encrustments are difficult to remove, and it is often necessary to shut down the installation and to empty it of water before mechanically or manually removing the said encrustments. Attempts have thus been made to introduce into the water, as active products, compounds having a biocidal and/or biostatic action which is capable of preventing the growth of the microorganisms and macroorganisms and their attachment to the surfaces in contact with water.

Numerous compounds termed biocides have been proposed and used for the treatment of water. Those most commonly employed in practice are halogens or halogenated inorganic or organic derivatives, such as chlorine, bromine, iodine, potassium chloride, hypochlorous acid and its sodium or calcium salts, hypobromous acid, the salts of dichloro- and trichloroisocyanuric acids, or halogenated hydantoins however, these compounds have the disadvantage of being corrosive and of forming, with the organic materials present in the water, chlorinated compounds which are highly toxic. It has also been proposed to use peroxygenated derivatives, phenols and phenol derivatives, heavy metals or organic derivatives thereof, formaldehyde, benzoic acid and benzoates for treatments by injection or by contact with a coating. However, the majority of these compounds are expensive, and their use in industrial installations which utilize large quantities of water is inconceivable. Moreover, many of them leave toxic or corrosive residues in the treated water.

The biocidal compounds are generally used in the form of a solution or dispersion in an aqueous phase which may contain organic solvents. In this case they are usually injected into the water to be treated. However, in certain cases, especially when these biocidal compounds are of low solubility in water, they are incorporated in a material, for example a paint, and the material containing the biocidal compound is applied to the surface to be protected, for example the hull of a ship, so as to treat the water in contact with the surface to be protected.

Generally, in order to be suitable for use in an appropriate fashion in a process for the treatment of industrial water, in particular in an open-circuit installation, a biocidal compound must have the properties of:

preventing the corrosion of surfaces in contact with the water, whether this corrosion derives from chemical products present in the water, such as $CO_2$, or from the biological film, preventing the formation of the biological film, eliminating or preventing the attachment of the macroorganisms, and leaving no toxic or corrosive residue in the water after use, so as to conserve the flora and fauna downstream of the industrial installation.

According to the present invention it has been found that amines, more specifically a particular mixture of polyamines, have all of the above properties, and that they make it possible advantageously to remove macroorganisms, more particularly molluscs, from surfaces in contact with water. More specifically they make it possible to eliminate the problem posed by zebra mussels or Dreissena in industrial installations in which water circulates in an open circuit, such as the cooling installations in thermal or nuclear power stations.

The subject of the present invention is therefore a process for the treatment of water and of surfaces in contact with the latter in order to prevent the attachment of and/or to destroy macroorganisms, in particular molluscs, on the surfaces in contact with the water, in which process at least one active biocidal and/or biostatic product is employed which is injected into the water and/or applied to the said surfaces, characterized in that the active product(s) used comprise(s) at least one polyamine of formula I:

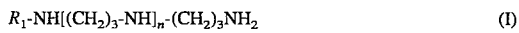

$$R_1\text{-NH[(CH}_2)_3\text{-NH]}_n\text{-(CH}_2)_3\text{NH}_2 \qquad (I)$$

in which formula $R_1$ is a $C_8$–$C_{22}$ alkyl or alkenyl radical and n is an integer between 0 and 3 (inclusive), and/or at least one monoamine of formula II:

$$R_2\text{NH}_2 \qquad (II)$$

in which formula $R_2$ is a $C_8$–$C_{22}$ alkyl or alkenyl radical.

According to the invention, the active product of formula I used is more particularly a mixture containing firstly at least one polyamine of formula I in which $R_1$ is a dodecyl radical, and/or at least one polyamine of formula I in which $R_1$ is a tetradecyl radical, and secondly at least one polyamine of formula I in which $R_1$ is an octadecenyl radical. This mixture may also contain other monoamines and/or polyamines.

According to the present invention, the amines and polyamines are used as such and not in the form of salts.

According to the present invention, the active product (s) may advantageously be injected into the water. According to the invention, the injection into the water of the active product(s) can be made, into the water to be treated, continuously or intermittently. In the first case, an amount required in order to obtain a concentration of between 0.01 and 1.5 ppm of product(s) of formula(e) I and/or II per liter of water may be suitable with regard to the treated surfaces. In the second case, daily injections of product(s) of formula(e) I and/or II such as to obtain a concentration of the order of 6 mg/l for 1.5 hours may bring about the eradication of a population of Dreissena in one month. The required concentrations of active product (s) of formula (e) I and/or II depend on the macroorganisms to be removed, on the size and nature of the surfaces in contact with the water, and on the flow of water, and may readily be determined by a person skilled in the art.

The treatment of the water by the active product(s) is advantageously carried out by injection into the water of a biocidal composition containing all of the active products of formula(e) I and/or II to be employed for the treatment. However, it is possible to envisage separate injections of the different active products to be employed, each injection being carried out with a partial biocidal composition. Further subjects of the invention are the total or partial biocidal compositions employed for the treatment process defined above.

These compositions are in practice preferably obtained by mixing polyamines derived from tallow and/or polyamines derived from a vegetable or animal oil containing olein with polyamines derived from coconut.

For injection into the water the compositions are preferably formulated as an emulsion, or better still a microemulsion, in an aqueous phase, since the amines of formula(e) I and/or II as such are not soluble in water. An emulsifying surfactant is advantageously used in order to emulsify the active product(s). This emulsifier advantageously comprises at least one polyoxyethylenated tertiary amine of formula III:

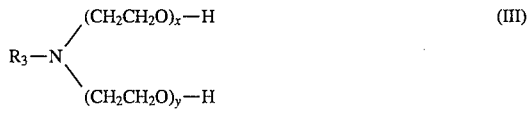

(III)

in which formula $R_3$ is a $C_8$–$C_{22}$ alkyl or alkenyl radical, preferably a hexadecyl, stearyl or oleyl radical, and x and y are integers such that x+y is between 5 and 50, preferably between 10 and 20. The emulsifier may make up from 5 to 45% by weight, preferably from 15 to 35% by weight, relative to the weight of the combination formed by the active product(s) of formula(e) I and/or II.

The aqueous phase may contain at least one organic solvent in addition to the water. This organic solvent is appropriately chosen from the group consisting of diethylene glycol, hexylene glycol, monopropylene glycol and an amino alcohol of formula IV:

$$HO\text{-}A\text{-}NR_4R_5 \quad (IV)$$

in which formula A is a $C_2$–$C_4$ linear or branched alkenyl radical and $R_4$ and $R_5$, which are identical or different, are H or a $C_1$–$C_3$ alkyl radical.

The aqueous phase of the emulsion, including the solvent if appropriate, may make up to 90% by weight of the said emulsion.

According to the present invention, it is also possible to treat the water by applying, to the surfaces in contact with the water, a coating containing at least one active product of formula(e) I and/or II, in particular a paint. According to a particular embodiment of such a paint, at least one active product of formula(e) I and/or II is mixed with a pulverulent filler, for example micronized silica, so as to obtain a pulverulent product which is subsequently introduced into a paint in the same way as a pigment. Another subject of the invention is the paint used for the implementation of this variant of the process.

According to the present invention, it has been found that the polyamines of formula I and the amines of formula II have an activity on the macroorganisms which attach themselves to the surfaces in contact with the water; these macroorganisms may be algae, serpulae, crustaceans, hydroids, bryozoa and hydrozoa, and more specifically molluscs, for example mussels, barnacles and clams. For simplification, this activity against macroorganisms will be denoted, in the remainder of the application, by the term "molluscicidal activity". It has also been found, according to the present invention, that this molluscicidal activity is particularly high when polyamines comprising a fatty chain $R_1$ which is a dodecyl (or lauryl) chain and/or a tetradecyl (or myristyl) chain are mixed with polyamines comprising an octadecenyl (or oleyl) fatty chain $R_1$. In effect, there is a synergetic reaction between these two types of polyamines, as shown by the examples given below. This preferred mixture of polyamines may additionally contain other polyamines, without the synergy being altered. This is the case in particular when use is made either of commercial polyamines of formula I in which the fatty chain is derived from coconut and contains, in addition to the polyamines of formula I having a $C_{12}$ and $C_{14}$ fatty chain, polyamines having a $C_8$, $C_{10}$, $C_{16}$, $C_{18}$, and monounsaturated $C_{18}$ radical $R_1$, or of commercial polyamines of formula I in which the fatty chain is derived from tallow and contains, in addition to the monounsaturated $C_{18}$ radical $R_1$, $C_{14}$, $C_{16}$ and $C_{18}$ radicals $R_1$, or of commercial polyamines of formula I derived from vegetable or animal oil containing olein, in which the fatty chain comprises, in addition to mono-unsaturated $C_{18}$ radicals $R_1$, $C_{14}$, $C_{16}$, mono-unsaturated $C_{16}$ and saturated $C_{18}$ radicals $R_1$, and in some cases dienic $C_{18}$ radicals $R_1$.

This mixture may also contain amines $R_2NH_2$, which are combined with the polyamines of formula I in the commercial products and whose radicals $R_2$ are generally the same as the radicals $R_1$ of the polyamines of formula I; in this case, the content of monoamines does not exceed 15% by weight.

Tests have shown that the biocidal composition according to the present invention makes it possible to remove striped mussels (Dreissena polymorpha) in a cooling installation of a thermal or nuclear power station, in which the water circulates in an open circuit, by injecting the composition into the water in the form of a microemulsion. Moreover, it has been found that the composition used in accordance with the invention makes it possible to prevent the attachment of molluscs to the surfaces in contact with the water. In effect, it has been observed in laboratory experiments that the composition used in accordance with the invention brings about an inhibition of the growth of the byssal filaments of striped mussels. A further observation has been the low adherence of barnacles and acorn-shells to the surfaces in contact with the water in the presence of the said biocidal composition.

It is known, furthermore, that the fatty-chain amines used have a stable film-forming effect and that, when injected into the water, they become attached in the form of a film to the surfaces in contact with the water. Consequently the necessary quantities of biocidal composition, when treatment is effected by injection, are low, because the film attached to the surfaces has a long-term action on the micro- and macroorganisms. This is not the case with chlorine and its derivatives (chlorine dioxide and organic chlorine compounds), the compounds which are most generally employed in the prior art, which do not become attached to the surfaces and which spread throughout the body of water. Consequently, according to the treatment process of the invention, the quantity of biocidal composition to be injected into the water depends more on the surfaces in contact with the water than on the flow of water in the installation. In particular, to treat a predetermined surface, it is possible first of all to introduce a relatively high concentration of biocidal composition according to the invention, so as to form the film on the surface, and subsequently to maintain a lower concentration of biocidal composition at the surface to be protected, in order to replenish the film and to act on the macroorganisms.

The biocidal composition used in accordance with the invention also makes it possible to prevent the formation of the biological film or to destroy it when it is formed and to prevent the corrosion caused by this biological film. It also has the anticorrosion action and antiscale action for which amines are known.

The biocidal and anticorrosion action of the biocidal composition used in accordance with the invention has been verified for numerous surfaces of steel, copper, ceramic, glass and plastics, for example.

Moreover, the biocidal composition used is not toxic. In fact, the life of the amines and polyamines in the medium treated is relatively short, and no toxic secondary products are formed. It has been found that the residual water leaving a cooling installation of a power station, the water of which is treated by the process according to the invention, has no toxic action on fish, in particular of young perch and bream.

The compositions used in accordance with the invention are prepared by mixing the constituents. In practice, a particularly appropriate composition is obtained by mixing at least one polyamine derived from coconut with at least one polyamine derived from tallow and/or at least one polyamine derived from a vegetable or animal oil containing olein.

The nonlimiting examples which are given below by way of illustration will enable better understanding of the invention.

EXAMPLES 1 to 82

Examples 1 to 82 relate to tests of the biocidal composition according to the invention in treatment by injection into the water.

A) Materials employed

1 Polyamines

Table I below gives the distribution of fatty chains in the commercial polyamines used. The first column of Table I gives the commercial name of the polyamine; for example, "tallow" denotes a polyamine whose fatty chain $R_1$ is derived from tallow, and "octyl" denotes a commercial polyamine derived from industrial octanoic acid.

TABLE I

| CHAINS | AVERAGE COMPOSITION OF FATTY CHAINS % by weight | | | | | | | |
|---|---|---|---|---|---|---|---|---|
| | C8 | C10 | C12 | C14 | C16 | C16.1* | C18 | C18.1* |
| Octyl or capryl | 98 | 2 | | | | | | |
| Decyl | | >90 | | | | | | |
| Dodecyl or lauryl | | 1–2 | 96–98 | 1–3 | | | | |
| Tetradecyl or myristyl | | | 2–4 | 92–96 | 2–4 | | | |
| Octadecyl or stearyl | | | | | 7–10 | | 90 | |
| Coconut | 3–7 | 5–7 | 48–54 | 18–20 | 9–14 | 8–12 | 2–8 | 4–6 |
| Tallow | | | | 4–5 | 30 | | 20–21 | 45 |
| Oleyl | | | 0–1 | 0–4 | 5–12 | 6 | 10 | 70–72 |

*C16.1 = hexadecenyl chain
C18.1 = octadecenyl chain

2 -Macroorganisms

Adult Dreissena (Dreissena polymorpha pallas) (18 to 23 mm in length) were collected in the Moselle. The molluscs are kept in the laboratory in dechlorinated and permanently aerated mains water suitable for drinking under the following conditions:

temperature: 18° C.±1° C.

pH: 7.6–8.2.

The Dreissena are fed daily with green algae of the genus Chlamydomonas, which have been frozen beforehand. The cubes of frozen algae are suspended above the experimentation vessels and distribute the algae gradually, as they melt.

B Methods

Mortality tests: The adult Dreissena (18–23 mm) are acclimatized to laboratory conditions for three days, during which they become attached to the support (a glass plate).

The experimental set-up consists of 12-liter vessels which are fed continuously (flow rate: 100 ml/min) with drinkable mains water which has been dechlorinated beforehand. The water in the vessels is permanently aerated and the medium is homogenized with a pump operating in closed circuit (flow rate: 6/min).

50 Dreissena make up the initial experimental sample for each support and each concentration tested. Each sample is subjected to daily injections of 90 minutes or 180 minutes so as to obtain concentrations of 2, 6 and 10 mg of composition per liter of water in the vessels, and this is repeated for each composition so as to determine the optimum efficacy.

The mortality is evaluated daily for one month; it is established when the Dreissena maintain their valves open and no longer respond to a tactile stimulus.

The control sample is subjected to the same experimental conditions but is maintained exclusively in dechlorinated drinkable mains water.

To determine the existence of a molluscicidal synergy for the mixture of two substances tested, the method used was that proposed by Ku F. C., Eismann P. C., Sylvestrowicz H. D., Mayer R. L. (1961), Appl. Microbiol. 9, 538–541, in order to determine the biostatic synergy. The formula used is as follows:

$$\frac{QA}{CA} + \frac{QB}{CB} = X$$

in which:

CA is the minimum molluscicida concentration of substance A

QA is the quantity of substance A in the minimum molluscicidal concentration of the mixture A/B CB is the minimum molluscicidal concentration of the substance B QB is the quantity of substance B in the minimum molluscicidal concentration of the mixture A/B.

When X=1, there is additivity of the effects; when X>1, there is antagonism; and, when X<1, there is synergy.

The compositions were prepared in the form of microemulsions by mixing one or more polyamines with 2-amino-2-methyl-1-propanol and an ethoxylated amine, as emulsifying surfactants, and water. Genamin® O-200 is an oleylamine which carries 20 units of ethylene oxide.

Table 2 gives, by way of comparison, the optimum molluscicidal concentrations for various polyamines used by themselves.

TABLE 2

| PRODUCTS | EXAMPLES | | | | | | | | |
|---|---|---|---|---|---|---|---|---|---|
| | 1 | 2 | 3 | 4 | 5 | 6 | 7 | 8 | 9 |
| | COMPOSITION IN % BY WEIGHT | | | | | | | | |
| N-octylamine | 10 | | | | | | | | |
| N-decylamine | | 10 | | | | | | | |
| N-dodecylamine | | | 10 | | | | | | |
| N-tetradecylamine | | | | 10 | | | | | |
| N-hexadecylamine | | | | | 10 | | | | |
| N-oleylamine | | | | | | 10 | | | |
| N-octadecylamine | | | | | | | 10 | | |
| N-erucidylamine | | | | | | | | 10 | |
| N-behenylamine | | | | | | | | | 10 |
| 2-amino-2-methyl-1-propanol | 2.5 | 2.5 | 2.5 | 2.5 | 2.5 | 2.5 | 2.5 | 2.5 | 2.5 |
| GENAMIN ® O-200 | 2.5 | 2.5 | 2.5 | 2.5 | 2.5 | 2.5 | 2.5 | 2.5 | 2.5 |
| WATER | 85 | 85 | 85 | 85 | 85 | 85 | 85 | 85 | 85 |
| MOLLUSCICIDAL CONCENTRATION | 10 | 8 | 8 | 10 | 11 | 9 | 11 | 13 | 14 |

| PRODUCTS | EXAMPLES | | | | | | | | |
|---|---|---|---|---|---|---|---|---|---|
| | 11 | 12 | 13 | 14 | 15 | 16 | 17 | 18 | 19 |
| | COMPOSITION IN % BY WEIGHT | | | | | | | | |
| N-octyl-1,3-propylenediamine | 10 | | | | | | | | |
| N-decyl-1,3-propylenediamine | | 10 | | | | | | | |
| N-dodecyl-1,3-propylenediamine | | | 10 | | | | | | |
| N-tetradecyl-1,3-propylenediamine | | | | 10 | | | | | |
| N-hexadecyl-1,3-propylenediamine | | | | | 10 | | | | |
| N-oleyl-1,3-propylenediamine | | | | | | 10 | | | |
| N-octadecyl-1,3-propylenediamine | | | | | | | 10 | | |
| N-coconut-1,3-propylenediamine | | | | | | | | 10 | |
| N-tallow-1,3-propylenediamine | | | | | | | | | 10 |
| 2-amino-2-methyl-1-propanol | 2.5 | 2.5 | 2.5 | 2.5 | 2.5 | 2.5 | 2.5 | 2.5 | 2.5 |
| GENAMIN ® O-200 | 2.5 | 2.5 | 2.5 | 2.5 | 2.5 | 2.5 | 2.5 | 2.5 | 2.5 |
| WATER | 85 | 85 | 85 | 85 | 85 | 85 | 85 | 85 | 85 |
| MOLLUSCICIDAL CONCENTRATION | 8 | 6 | 6 | 8 | 10 | 8 | 9 | 6 | 8.5 |

It can be seen from Table 2 that the various amines and diamines, used on their own, have a molluscicidal action.

Table 3 gives the molluscicidal action of various mixtures of diamines.

TABLE 3

| | EXAMPLES | | | | | | | | | |
|---|---|---|---|---|---|---|---|---|---|---|
| PRODUCTS | 20 | 21 | 22 | 23 | 24 | 25 | 26 | 27 | 28 | 29 |
| | COMPOSITION IN % BY WEIGHT | | | | | | | | | |
| N-dodecyl-1,3-propylene-diamine | 8 | 6 | 5 | 4 | 2 | 8 | 6 | 5 | 4 | 2 |
| N-tetradecyl-1,3-propylene-diamine | 2 | 4 | 5 | 6 | 8 | — | — | — | — | — |
| N-oleyl-1,3-propylene-diamine | — | — | — | — | — | 2 | 4 | 5 | 6 | 8 |
| 2-amino-2-methyl-1-propanol | 2.5 | 2.5 | 2.5 | 2.5 | 2.5 | 2.5 | 2.5 | 2.5 | 2.5 | 2.5 |
| GENAMIN ® O-200 | 2.5 | 2.5 | 2.5 | 2.5 | 2.5 | 2.5 | 2.5 | 2.5 | 2.5 | 2.5 |
| WATER | 85 | 85 | 85 | 85 | 85 | 85 | 85 | 85 | 85 | 85 |
| MOLLUSCICIDAL CONCENTRATION | 6.5 | 7 | 7 | 7.5 | 7.5 | 6.1 | 6.0 | 6.1 | 6.4 | 7.1 |
| VALUE of X | 1 | 1 | 1 | 1 | 1 | 0.96 | 0.90 | 0.89 | 0.91 | 0.96 |

| | EXAMPLES | | | | | | | | | |
|---|---|---|---|---|---|---|---|---|---|---|
| PRODUCTS | 30 | 31 | 32 | 33 | 34 | 35 | 36 | 37 | 38 | 39 |
| | COMPOSITION IN % BY WEIGHT | | | | | | | | | |
| N-dodecyl-1,3-propylene-diamine | — | — | — | — | — | — | — | — | — | — |
| N-tetradecyl-1,3-propylene-diamine | 8 | 6 | 5 | 4 | 2 | — | — | — | — | — |
| N-oleyl-1,3-propylene-diamine | 2 | 4 | 5 | 6 | 8 | 1 | 2 | 2 | 4 | 5 |
| N-coconut-1,3-propylene-diamine | — | — | — | — | — | 9 | 8 | 7 | 6 | 5 |
| 2-amino-2-methyl-1-propanol | 2.5 | 2.5 | 2.5 | 2.5 | 2.5 | 2.5 | 2.5 | 2.5 | 2.5 | 2.5 |
| GENAMIN ® O-200 | 2.5 | 2.5 | 2.5 | 2.5 | 2.5 | 2.5 | 2.5 | 2.5 | 2.5 | 2.5 |
| WATER | 85 | 85 | 85 | 85 | 85 | 85 | 85 | 85 | 85 | 85 |
| MOLLUSCICIDAL CONCENTRATION | 7.6 | 7.1 | 7.1 | 7.4 | 7.7 | 5.9 | 6.0 | 5.9 | 5.6 | 5.7 |
| VALUE of X | 0.95 | 0.88 | 0.89 | 0.92 | 0.96 | 0.97 | 0.96 | 0.94 | 0.88 | 0.88 |

| | EXAMPLES | | | | | | | | | |
|---|---|---|---|---|---|---|---|---|---|---|
| PRODUCTS | 40 | 41 | 42 | 43 | 44 | 45 | 46 | 47 | 48 | 49 | 50 |
| | COMPOSITION IN % BY WEIGHT | | | | | | | | | |
| N-coconut-1,3-propylene-diamine | 4 | 3 | 2 | 9 | 8 | 7 | 6 | 5 | 4 | 3 | 2 |
| N-oleyl-1,3-propylene-diamine | 6 | 7 | 8 | — | — | — | — | — | — | — | — |
| N-tallow-1,3-propylene-diamine | — | — | — | 1 | 2 | 3 | 4 | 5 | 6 | 7 | 8 |
| 2-amino-2-methyl-1-propanol | 2.5 | 2.5 | 2.5 | 2.5 | 2.5 | 2.5 | 2.5 | 2.5 | 2.5 | 2.5 | 2.5 |
| GENAMIN ® O-200 | 2.5 | 2.5 | 2.5 | 2.5 | 2.5 | 2.5 | 2.5 | 2.5 | 2.5 | 2.5 | 2.5 |
| WATER | 85 | 85 | 85 | 85 | 85 | 85 | 85 | 85 | 85 | 85 | 85 |
| MOLLUSCICIDAL CONCENTRATION | 5.9 | 6.1 | 6.4 | 5.9 | 6.1 | 6.2 | 6.1 | 6.4 | 6.8 | 7.2 | 7.5 |
| VALUE of X | 0.90 | 0.91 | 0.94 | 0.95 | 0.96 | 0.94 | 0.89 | 0.91 | 0.93 | 0.95 | 0.96 |

This table shows that the mixture of dodecylpropylenediamine and of tetradecylpropylenediamine has no synergetic effect on the molluscicidal action, but that, when the mixture contains an octadecenyl (C81.1) propylenediamine, there is synergy (X is less than 1).

Table 4 indicates the molluscicidal concentrations in the presence of triamines and tetramines on their own (Examples 52 to 55) or as a mixture with other polyamines (Examples 51 and 53 to 65).

TABLE 4

| | EXAMPLES | | | | | | |
|---|---|---|---|---|---|---|---|
| PRODUCTS | 51 | 52 | 53 | 54 | 55 | 56 | 57 |
| | COMPOSITION IN % BY WEIGHT | | | | | | |

TABLE 4-continued

| PRODUCTS | | | | | | | |
|---|---|---|---|---|---|---|---|
| N-coconut-1,3-propylene-diamine | | | | | | 5 | 5 |
| N-coconut-[NH(CH$_2$)$_3$]$_2$NH$_2$ | 10 | | | | | | |
| N-oleyl-[NH(CH$_2$)$_3$]$_2$NH$_2$ | | 10 | | | | 5 | |
| N-tallow-[NH(CH$_2$)$_3$]$_2$NH$_2$ | | | 10 | | | | |
| N-coconut-[NH(CH$_2$)$_3$]$_3$NH$_2$ | | | | 10 | | | |
| N-oleyl-[NH(CH$_2$)$_3$]$_3$NH$_2$ | | | | | 10 | | 5 |
| 2-amino-2-methyl-1-propanol | 2.5 | 2.5 | 2.5 | 2.5 | 2.5 | 2.5 | 2.5 |
| GENAMIN ® O-200 | 2.5 | 2.5 | 2.5 | 2.5 | 2.5 | 2.5 | 2.5 |
| WATER | 85 | 85 | 85 | 85 | 85 | 85 | 85 |
| MOLLUSCICIDAL CONCENTRATION | 6.5 | 7 | 8 | 6 | 7 | 6.4 | 6.2 |
| VALUE of X | — | — | — | — | — | 0.96 | 0.93 |

| | EXAMPLES | | | | | | | |
|---|---|---|---|---|---|---|---|---|
| | 58 | 59 | 60 | 61 | 62 | 63 | 64 | 65 |
| PRODUCTS | COMPOSITION IN % BY WEIGHT | | | | | | | |
| N-coconut-1,3-propylene-diamine | | | | | 8 | 2 | | 3 |
| N-oleyl-1,3-propylenediamine | 5 | 5 | | 4 | | | 8 | |
| N-coconut-[NH(CH$_2$)$_3$]$_2$NH$_2$ | 5 | | 5 | 6 | | | 2 | |
| N-coconut-[NH(CH$_2$)$_3$]$_3$NH$_2$ | | 5 | | | | | | 7 |
| N-oleyl-[NH(CH$_2$)$_3$]$_3$NH$_2$ | | | 5 | | 2 | 8 | | |
| 2-amino-2-methyl-1-propanol | 2.5 | 2.5 | 2.5 | 2.5 | 2.5 | 2.5 | 2.5 | 2.5 |
| GENAMIN ® O-200 | 2.5 | 2.5 | 2.5 | 2.5 | 2.5 | 2.5 | 2.5 | 2.5 |
| WATER | 85 | 85 | 85 | 85 | 85 | 85 | 85 | 85 |
| MOLLUSCICIDAL CONCENTRATION | 6.3 | 6.1 | 6.4 | 6.1 | 5.9 | 6.8 | 6.4 | 6.9 |
| VALUE of X | 0.93 | 0.94 | 0.92 | 0.91 | 0.94 | 0.93 | 0.93 | 0.97 |

Table 4 shows that there is also synergy when the oleyl polyamine is a triamine or a tetramine.

The tests compiled in Table 5 were carried out in the presence of different solvents and different emulsifying surfactants.

TABLE 5

| PRODUCTS | EXAMPLES | | | | | | | |
|---|---|---|---|---|---|---|---|---|
| | 66 | 67 | 68 | 69 | 70 | 71 | 72 | 73 |
| | COMPOSITION IN % BY WEIGHT | | | | | | | |
| N-coconut-1,3-propylene-diamine | 4 | 4 | 4 | 4 | 4 | 4 | 4 | 4 |
| N-oleyl-1,3-propylene-diamine | 6 | 6 | 6 | 6 | 6 | 6 | 6 | 6 |
| DIETHYLENE GLYCOL | 10 | | | | | | | |
| HEXYLENE GLYCOL | | 10 | | | | 10 | 10 | |
| MONOPROPYLENE GLYCOL | | | 10 | | | | | 10 |
| 2-amino-2-methyl-1-propanol | 2.5 | 2.5 | 2.5 | 2.5 | 2.5 | 2.5 | 2.5 | 2.5 |
| GENAMIN ® S-200* | 2.5 | 2.5 | 2.5 | | | | | |
| GENAMIN ® O-250* | | | | 2.5 | | 2.5 | | |
| GENAMIN ® T-200* | | | | | 2.5 | | | 2.5 |
| GENAMIN ® T-250* | | | | | | | 2.5 | |
| WATER | 75 | 75 | 75 | 85 | 85 | 75 | 75 | 75 |
| MOLLUSCICIDAL CONCENTRATION | 6 | 6 | 6 | 6.2 | 6.1 | 6.2 | 6.2 | 6.1 |
| VALUE of X | 0.91 | 0.91 | 0.91 | 0.94 | 0.93 | 0.94 | 0.94 | 0.93 |

| PRODUCTS | EXAMPLES | | | | | | | | |
|---|---|---|---|---|---|---|---|---|---|
| | 74 | 75 | 76 | 77 | 78 | 79 | 80 | 81 | 82 |
| | COMPOSITION IN % BY WEIGHT | | | | | | | | |
| N-coconut-1,3-propylene-diamine | 4 | 4 | 4 | 4 | 4 | 4 | 4 | 4 | 4 |
| N-oleyl-1,3-propylene-diamine | 6 | 6 | 6 | 6 | 6 | 6 | 4 | 6 | 6 |
| DIETHYLENE GLYCOL | | | | 50 | 50 | 50 | 50 | 50 | 50 |
| HEXYLENE GLYCOL | | | | | | | 2 | 2.5 | |
| MONOPROPYLENE GLYCOL | | | | | | 2 | 0.5 | 0.5 | |
| 2-amino-2-methyl-1-propanol | 2.5 | 2.5 | 2.5 | 2.5 | 2.5 | 0.5 | | | 2.5 |
| 2-diethylamino-1-ethanol | | 2.5 | | | 2.5 | | | | |
| GENAMIN ® S-200* | 2.5 | | | 2.5 | | | | | 2.5 |
| GENAMIN ® O-250* | | | 2.5 | | | | | 2.5 | |
| GENAMIN ® T-200* | | | | | | | 2.5 | 2.5 | |
| GENAMIN ® T-250* | 85 | 85 | 85 | 35 | 35 | 35 | 35 | 35 | 35 |
| WATER | | | | | | | | | |
| MOLLUSCICIDAL CONCENTRATION | 6.2 | 6 | 6.1 | 6.2 | 6 | 6.2 | 6.2 | 6.1 | 6.2 |
| VALUE of X | 0.94 | 0.91 | 0.93 | 0.94 | 0.91 | 0.94 | 0.94 | 0.93 | 0.94 |

*Genamin S-200: soya amine containing 20 units of ethylene oxide
Genamin O-250: olein amine containing 25 units of ethylene oxide
Genamin T-200: tallow amine containing 20 units of ethylene oxide
Genamin T-250: tallow amine containing 25 units of ethylene oxide Table 5 shows that the different solvents and the different emulsifying surfactants have virtually no effect on the molluscicidal action of the polyamines.

EXAMPLES 83 to 138

Examples 83 to 138 relate to tests of a bioactive paint for treatment by application to the surfaces in contact with the water.

A) Method

A series of bioactive paints was made which contained compositions based on long-chain amines, which were introduced into a coating composition corresponding to the following formulation, expressed by dry weight:

| | |
|---|---|
| Vinyl resin | 27 parts by weight |
| Shellac | 33 parts by weight |
| Tricresyl phosphate | 10 parts by weight |
| Red iron oxide | 5 parts by weight |
| Bioactive filler* | 25 parts by weight |

*Bioactive filler = 50% by weight of amines + 50% by weight of Sylobloc 45 ® (micronized silica)

The bioactive filler is a powder obtained by mixing the amine, in the liquid state, with Sylobloc 45® in a high-shear turbine.

The composition of the bioactive filler is represented by compositions 83 to 138. The bioactive coating was obtained by incorporating the bioactive filler into the formulation above. The components of the formulation were dispersed beforehand, using a high-shear turbine, with a mixture of 30% by weight of solvent comprising xylene/Solvesso 100 (72/28 by weight), at a speed of 20,000 revolutions per minute so as to obtain a fine and homogeneous dispersion, before introduction of the bioactive filler.

150×®×1.5 mm steel plates were sanded on both sides and then coated with each bioactive formulation in two layers representing, after drying, a total layer of 80 microns in thickness; the control plates were treated in the same way, although the formulation contained only "Sylobloc 45 " silica as filler, with no bioactive amine.

Two series of plates were then immersed in the sea in the sub-tropical zone, suspended by nylon threads at a depth of 1 metre in one case and 10 metres in the other case, in order to determine the anti-fouling properties. The immersion tests were carried out for an initial period of 1 month in January: the plates were then withdrawn and compared with the control plates; after weighing, the deposits attached to the plates were removed for identification and counting of the species deposited per $m^2$. A new series of coated plates was immersed under the same conditions for a period of three months with three repeats in February, May, August and October, and then examined again by comparison with the control plates.

Table 6 indicates the most important of the various species which became attached principally to the series of plates immersed as controls.

TABLE 6

| | | | SPECIES | | | |
|---|---|---|---|---|---|---|
| ALGAE | BRYOZOA | (POLYCHAETES) SERPULAE | (CIRRIPEDES) CRUSTACEANS | ASCIDIANS | AMPHIPODS | HYDROZOA |
| Rhizoclonium riparium and Enteromorpha prolifera | Bugula neritina | Hydroides norvegica | Balanus amphitrite variegatus trigonus | Cyona intestinalis | Ericthnius pugnax | Tubularia mesembryanthenum |

B Results

The inhibitory activity of the various compositions with regard to marine fouling was evaluated as a function of the weight and number of the various species deposited on the experimental plates immersed close to the surface and at a depth, at the end of the various periods of immersion. Table 7 shows the efficacy, expressed in %, for each composition of bioactive filler introduced into the coating formula. The efficacy is calculated as follows: the weight of microorganisms on each treated plate and on the control plate is measured, and the weight difference is calculated. The efficacy is expressed in per cent. The value given is the arithmetic mean of the values obtained.

It is evident that the mixtures of polyamines derived from coconut with polyamines derived from tallow or oleyl polyamines are more effective as marine anti-fouling agents than the pure amines taken individually, as shown by the results given in Table 7.

TABLE 7

| PRODUCTS | EXAMPLES | | | | | | | | | |
|---|---|---|---|---|---|---|---|---|---|---|
| | 83 | 84 | 85 | 86 | 87 | 88 | 89 | 90 | 91 | 92 |
| | COMPOSITION IN % BY WEIGHT | | | | | | | | | |
| N-octylamine | 50 | | | | | | | | | |
| N-decylamine | | 50 | | | | | | | | |
| N-tetradecylamine | | | 50 | | | | | | | |
| N-hexadecylamine | | | | 50 | | | | | | |
| N-oleylamine | | | | | 50 | | | | | |
| N-octadecylamine | | | | | | 50 | | | | |
| N-octyl-1,3-propylene-diamine | | | | | | | 50 | | | |
| N-decyl-1,3-propylene-diamine | | | | | | | | 50 | | |
| N-dodecyl-1,3-propylene-diamine | | | | | | | | | 50 | |
| N-tetradecyl-1,3-propylenediamine | | | | | | | | | | 50 |
| Sylobloc 45 | 50 | 50 | 50 | 50 | 50 | 50 | 50 | 50 | 50 | 50 |
| EFFICACY in % | 5 | 10 | 30 | 20 | 17 | 15 | 5 | 12 | 30 | 25 |

| PRODUCTS | EXAMPLES | | | | | | | | | |
|---|---|---|---|---|---|---|---|---|---|---|
| | 93 | 94 | 95 | 96 | 97 | 98 | 99 | 100 | 101 | 102 |
| | COMPOSITION IN % BY WEIGHT | | | | | | | | | |
| N-hexadecyl-1,3-propylenediamine | 50 | | | | | | | | | |
| N-oleyl-1,3-propylenediamine | | 50 | | | 50 | | | | | |
| N-octadecyl-1,3-propylenediamine | | | 50 | | | | | | | |
| N-coconut-1,3-propylenediamine | | | | 50 | | | | | | |
| N-tallow-1,3-propylenediamine | | | | | | 50 | | | | |
| N-dodecyl-1,3-propylenediamine | | | | | | | 40 | 30 | 25 | 20 |
| N-tetradecyl-1,3-propylenediamine | | | | | | | 10 | 20 | 25 | 30 |
| Sylobloc 45 | 50 | 50 | 50 | 50 | 50 | 50 | 50 | 50 | 50 | 50 |
| EFFICACY in % | 15 | 20 | 10 | 25 | 20 | 15 | 20 | 20 | 25 | 20 |

| PRODUCTS | EXAMPLES | | | | | | | | | |
|---|---|---|---|---|---|---|---|---|---|---|
| | 103 | 104 | 105 | 106 | 107 | 108 | 109 | 110 | 111 | |
| | COMPOSITION IN % BY WEIGHT | | | | | | | | | |
| N-dodeceyl-1,3-propylenediamine | 10 | 40 | 30 | 25 | 20 | | | | | |
| N-tetradecyl-1,3-propylenediamine | 40 | | | | | | 40 | 30 | 25 | 20 |
| N-oleyl-1,3-propylenediamine | | 10 | 20 | 25 | 30 | 10 | 20 | 25 | 30 | |
| Sylobloc 45 | 50 | 50 | 50 | 50 | 50 | 50 | 50 | 50 | 50 | |
| EFFICACY in % | 25 | 50 | 55 | 50 | 40 | 40 | 45 | 45 | 40 | |

| PRODUCTS | EXAMPLES | | | | | | | | | |
|---|---|---|---|---|---|---|---|---|---|---|
| | 112 | 113 | 114 | 115 | 116 | 117 | 118 | 119 | 120 | |
| | COMPOSITION IN % BY WEIGHT | | | | | | | | | |
| N-coconut-1,3-propylenediamine | 45 | 40 | 30 | 25 | 20 | 5 | 45 | 40 | 35 | |
| N-oleyl-1,3-propylenediamine | | | | | | | 5 | 10 | 15 | |
| N-tallow-1,3-propylenediamine | 5 | 10 | 20 | 25 | 30 | 45 | | | | |
| Sylobloc 45 | 50 | 50 | 50 | 50 | 50 | 50 | 50 | 50 | 50 | |
| EFFICACY in % | 50 | 45 | 55 | 50 | 40 | 37 | 45 | 30 | 55 | |

| PRODUCTS | EXAMPLES | | | | | | | | | |
|---|---|---|---|---|---|---|---|---|---|---|
| | 121 | 122 | 123 | 124 | 125 | 126 | 127 | 128 | 129 | |
| | COMPOSITION IN % BY WEIGHT | | | | | | | | | |
| N-coconut-1,3-propylenediamine | | 30 | 25 | 20 | 15 | 10 | | | | |

TABLE 7-continued

| PRODUCTS | | | | | | | | | |
|---|---|---|---|---|---|---|---|---|---|
| N-oleyl-1,3-propylenediamine | 20 | 15 | 30 | 35 | 40 | | | | |
| N-dodecyl-[NH(CH$_2$)$_3$]$_{2-NH2}$ | | | | | | 50 | | | |
| N-coconut-[NH(CH$_2$)$_3$]$_{2-NH2}$ | | | | | | | 50 | | |
| N-oleyl-[NH(CH$_2$)$_3$]$_{2-NH2}$ | | | | | | | | 50 | |
| N-tallow-[NH(CH$_2$)$_3$]$_{2-NH2}$ | | | | | | | | | 50 |
| Sylobloc 45 | 50 | 50 | 50 | 50 | 50 | 50 | 50 | 50 | 50 |
| EFFICACY in % | 55 | 65 | 45 | 40 | 40 | 40 | 30 | 30 | 25 |

| | EXAMPLES | | | | | | | | |
|---|---|---|---|---|---|---|---|---|---|
| | 130 | 131 | 132 | 133 | 134 | 135 | 136 | 137 | 138 |
| PRODUCTS | COMPOSITION IN % BY WEIGHT | | | | | | | | |
| N-coconut-1,3-propylenediamine | | | 25 | 25 | | | | | |
| N-oleyl-1,3-propylenediamine | | | | | 25 | 25 | | | 20 |
| N-coconut-[NH(CH$_2$)$_3$]$_{2-NH2}$ | | | | | | 25 | | 25 | 30 |
| N-oleyl-[NH(CH$_2$)$_3$]$_{2-NH2}$ | | | | 25 | | | | | |
| N-coconut-[NH(CH$_2$)$_3$]$_{3-NH2}$ | 50 | | | | | | 25 | | |
| N-oleyl-[NH(CH$_2$)$_3$]$_{3-NH2}$ | | 50 | | | 25 | | | 25 | |
| N-tallow-[NH(CH$_2$)$_3$]$_{3-NH2}$ | 50 | | | | | | | | |
| Sylobloc 45 | 50 | 50 | 50 | 50 | 50 | 50 | 50 | 50 | 50 |
| EFFICACY in % | 35 | 30 | 35 | 50 | 45 | 45 | 40 | 40 | 50 |

After a period of one month, the mean percentage mortality remains very low in the control group, indicating that the mortality recorded in the groups exposed to the treatment according to the invention does indeed result from the molluscicidal action tested.

I claim:

1. A biocidal or biostatic composition containing an active agent comprising a mixture of amines containing at least one polyamine of the formula (I)

$$R_1\text{-NH}[(CH_2)_3\text{-NH}]_n\text{-}(CH_2)_3NH_2 \quad (I)$$

in which n is an integer from 0 to 3 and R$_1$ is a dodecyl radical or at least one polyamine of formula (I) wherein R$_1$ is an tetradecyl radical, or a mixture thereof, at least one polyamine of formula (I) wherein R$_1$ is an octadecenyl radical and at least one monoamine of the formula (II):

$$R_2NH_2 \quad (II)$$

wherein R$_2$ is an octadecenyl radical.

2. The composition according to claim 1 wherein said polyamines are derived from at least one of tallow, or vegetable or animal oil containing olein with at least one of said polyamines being derived from coconut.

3. The composition according to claim 1 wherein said active agent contains not more than 15% by weight of said at least one amine of formula (II).

4. The composition according to claim 1 wherein said composition is an aqueous emulsion.

5. The composition according to claim 4 further comprising an emulsifier comprising at least one polyoxyethylenated tertiary amine of formula (III):

$$R_3-N\begin{matrix}(CH_2CH_2O)_x-H\\(CH_2CH_2O)_y-H\end{matrix} \quad (III)$$

in which formula R$_3$ is a C$_8$–C$_{22}$ alkyl or alkenyl radical and x and y are integers such that (x+y) is from 5 to 50.

6. The composition according to claim 5 wherein the emulsifier is present in an amount of from 5 to 45% by weight relative to said active agent.

7. The composition according to claim 4 wherein the aqueous phase of said emulsion contains at least one organic solvent selected from the group consisting of at least one organic solvent selected from the group consisting of diethylene glycol, hexylene glycol, monopropylene glycol and an amino alcohol of formula IV:

$$\text{HO-A-N}R_4R_5 \quad (IV)$$

in which A is a C$_2$–C$_4$ linear or branched alkenyl radical and R$_4$ and R$_5$, which are identical or different, are H or a C$_1$–C$_3$ alkyl radical.

* * * * *